(12) United States Patent
Müller et al.

(10) Patent No.: US 8,114,392 B2
(45) Date of Patent: Feb. 14, 2012

(54) METHOD FOR SMOOTHING FIBERS CONTAINING KERATIN

(75) Inventors: Burkhard Müller, Hamburg (DE); Aaltje Schellin, Hamburg (DE); Inge Neubüser, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/942,193

(22) Filed: Nov. 9, 2010

(65) Prior Publication Data

US 2011/0048447 A1    Mar. 3, 2011

Related U.S. Application Data

(60) Division of application No. 11/297,707, filed on Dec. 8, 2005, now abandoned, which is a continuation of application No. PCT/EP2004/009151, filed on Aug. 14, 2004.

(30) Foreign Application Priority Data

Aug. 23, 2003 (DE) ................................. 103 38 883

(51) Int. Cl.
*A61Q 5/00* (2006.01)
*A45D 7/02* (2006.01)

(52) U.S. Cl. ..................... 424/70.28; 424/70.1; 132/206

(58) Field of Classification Search .................. None
See application file for complete search history.

(56) References Cited

U.S. PATENT DOCUMENTS

| | | | |
|---|---|---|---|
| 1,985,424 A | 12/1934 | Piggott | |
| 2,016,962 A | 10/1935 | Flint et al. | |
| 2,703,798 A | 3/1955 | Schwartz | |
| 4,865,774 A | 9/1989 | Fabry et al. | |
| 4,931,218 A | 6/1990 | Schenker et al. | |
| 5,060,680 A | 10/1991 | Akhtar | |
| 5,294,230 A | 3/1994 | Wu et al. | |
| 5,294,726 A | 3/1994 | Behler et al. | |
| 5,312,932 A | 5/1994 | Behler et al. | |
| 5,322,957 A | 6/1994 | Fabry et al. | |
| 5,484,531 A | 1/1996 | Kuehne et al. | |
| 5,773,595 A | 6/1998 | Weuthen et al. | |
| 6,125,856 A | 10/2000 | Yamashita | |
| 6,235,913 B1 | 5/2001 | Raths et al. | |
| 7,332,466 B2 | 2/2008 | Schmid et al. | |
| 2003/0009834 A1 | 1/2003 | Ascione et al. | |

FOREIGN PATENT DOCUMENTS

| | | |
|---|---|---|
| EP | 0361391 A2 | 4/1990 |
| EP | 0690044 A2 | 1/1996 |
| GB | 2114616 A | 8/1983 |
| GB | 2197352 A | 5/1988 |
| JP | 60021704 A | 2/1985 |
| WO | 9206984 A1 | 4/1992 |
| WO | 9725964 A1 | 7/1997 |
| WO | 9917719 A1 | 4/1999 |

OTHER PUBLICATIONS

McMullen, R. et al. "Thermal degradation of hair. I. Effect of curling irons." Journal of Cosmetic Science, vol. 49, Jul./Aug. 1998, pp. 223-244.

McMullen, R. et al. "Thermal degradation of hair. II. Effect of selected polymers and surfactants." Journal of Cosmetic Science, vol. 49, Jul./Aug. 1998, pp. 245-256.

Society of Cosmetics Chemists. Monograph, Surfactants. SCC Monograph Series, 1997.

Biswas, A.K. et al. "Surface-Active Properties of Sodium Salts of Sulfated Fatty Acid Monoglycerides." J. Am. Oil. Chem. Soc., vol. 37, Apr. 1960, pp. 171-175.

Ahmed, Fahim U. "Efficient Synthesis of Fatty Monoglyceride Sulfates from Fatty Acids and Fatty Acid Methyl Esters." J. Am. Oil. Chem. Soc., vol. 67I, No. 1, Jan. 1990, pp. 8-14.

Biermann et al. "Alkyl Polyglucosides—Technology and Properties." Starch, vol. 45, No. 8, 1993, pp. 281-288.

Salka, Barry. "Alkyl Polyglycosides: Properties and Applications." Cosmetics & Toiletries, vol. 108, Mar. 1993, pp. 89-94.

Kahre, J. et al. "Alkyl Polyglycacides—A New Concept for Care and Tolerance in Cosmetics." SOFW-Journal, vol. 121, Aug. 1995, p. 598-611.

Alexander, Philip. "Permanent Waving." Manufacturing Chemist, vol. 59, No. 5, May 1988, pp. 61-64.

*Primary Examiner* — Jyothsna Venkat
(74) *Attorney, Agent, or Firm* — David P. LeCroy

(57) ABSTRACT

Method for smoothing fibers containing keratin, in particular human hair. Fibers are subjected to a thermal treatment and to a treatment with an agent containing at least one conditioning compound selected from cationic polymers, quaternary ammonium compounds, silicones and protein hydrolyzates. The invention also relates to the use of an agent containing at least one of the conditioning compounds concerned in said method for smoothing fibers containing keratin. The inventive method achieves an excellent, uniform smoothing of the fibers, which are also conditioned.

16 Claims, No Drawings

METHOD FOR SMOOTHING FIBERS CONTAINING KERATIN

CROSS REFERENCE TO RELATED APPLICATIONS

The present application is a divisional application of U.S. patent application Ser. No. 11/297,707 filed on 8 Dec. 2005 now abandoned, which is a continuation of International Patent Application No. PCT/EP2004/009151 filed 14 Aug. 2004, incorporated herein by reference, which claims priority to German Patent Application No. DE 103 38 883.4, filed 23 Aug. 2003, incorporated herein by reference.

BACKGROUND OF THE INVENTION

Field of the Invention

The invention relates to a method for smoothing fibers containing keratin, especially human hair, as well as to the use of an agent containing at least one conditioning compound, selected from among cationic polymers, quaternary ammonium compounds, silicones and protein hydrolyzates in said method for smoothing fibers containing keratin.

In principle, all animal hair, e.g., wool, horsehair, angora hair, furs, feathers and the products and textiles made from these are fibers containing keratin. The invention is preferably used for smoothing curly human hair and wigs made therefrom.

A permanent shaping of fibers containing keratin is normally done in such a way that one shapes the fiber mechanically and then fixes the shape with the help of suitable means. Before and/or after said shaping, one treats the fibers with a keratin-reducing preparation. The fiber is then rinsed and treated with a preparation containing oxidizing agent. It is then rinsed and freed of the shaping means (curlers, papillotes). If a mercaptan is used as a keratin-reducing component, e.g., ammonium thioglycolate, part of the disulfide bridges of the keratin molecule is cleaved to —SH— groups, resulting in a softening of the keratin fiber. During the subsequent oxidative fixation, the disulfide bridges are bonded again so that the keratin structure gets fixed in the given shape. Alternatively, it is known that sulfite can be used for shaping hair as a keratin reducing component in place of mercaptan. By means of hydrogen sulfite solutions and/or sulfite solutions and/or disulfite solutions, the disulfide bridges of the keratin molecules are split in a sulfitolysis according to the equation

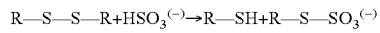

and in this way the keratin fibers are softened.

Reducing agents containing hydrogen sulfite, sulfite or disulfite do not possess the strong smell of the agents containing mercaptan. The cleavage can be undone, as described earlier, in a fixation step with the help of an oxidizing agent under the formation of new disulfide bridges.

The permanent smoothing of fibers containing keratin is thus achieved by mechanical shaping and the use of keratin-reducing and oxidizing compounds. In a corresponding process, for smoothing curly human hair and the wigs made thereof, the curly hair is wound on a curler with a large diameter of normally more than 15 mm or the hair is combed smooth under the effect of a keratin-reducing compound. Another possibility of smoothing the hair is with the help of a hot iron. However, the heat treatment of the hair permanently changes the structure of the fiber containing keratin while smoothing (see R. McMullen et al., *J. Cosmet. Sci.*, Vol. 49 (1998), pp. 223-244). This change of the fiber structure should be counteracted by taking appropriate steps.

As per JP-A-60 21704 it is advantageous, to apply an oil-based cream on the hair before the heat treatment with a hot iron. The cream protects the structure of the fiber containing keratin during the heat treatment and ensures a uniform smoothing. The use of cationic polymers, silicones, quaternary ammonium compounds and protein hydrolyzates is not mentioned in this document.

The publication EP-A1-1 099 391 teaches a method for hair smoothing and conditioning, in which the fibers are heat-treated or ironed with a hot iron after the reductive cleavage of the disulfide bridges. Before using the hot iron, a conditioner containing a polypeptide is applied on the hair and left on the hair. The chemical reaction of the polymeric protein molecules with the hair fiber during smoothing protects the hair fiber from the effect of the heat (see also R. McMullen et al., *J. Cosmet. Sci.*, Vol. 49 (1998), pp. 245-254) and counteracts the structural change of the hair fiber. However, the use of a conditioner in said method is disadvantageous. Due to the heat treatment of the fibers in the presence of a conditioner, especially in the presence of polymers having a conditioning effect, e.g., polyacrylic acid and its derivatives, the hair fibers stick together to form hair bundles during smoothing. This bundling can be irreversible and hence can negatively influence the grip, appearance and combability of the hair on a permanent basis.

Further, there are undesired chemical reactions of the conditioner, induced by the heat treatment, in the form of decomposition products or conversion with the other components of the formulation. The conditioning compounds lose their effect as a result of heat treatment on one hand, and on the other hand, the decomposition products or products of a reaction with the other components of the formulation can be physiologically critical.

Generally, the known smoothing processes with heat treatment have the further disadvantage that the fiber containing keratin gets electrostatically charged. Moreover, the result of the smoothing in the known methods needs further improvement regarding the degree of smoothing and the uniformity of smoothing.

The objective of the invention is thus to provide a smoothing method for fibers containing keratin, especially for human hair, which produces a better smoothing result, protects the structure of the hair and conditions the hair.

It was surprisingly found that this objective could be attained by the method described herein below. In the method according to the present invention, formulations are used, which contain at least one compound with a conditioning effect, selected from cationic polymers, quaternary ammonium compounds, silicones and protein hydrolyzates.

The publication WO-A1-93/105757 discloses a holding agent for a permanent hair shaping, which, along with an oxidizing agent, also contains at least one cationic polymer as well as at least one nonionic and at least one amphoteric surfactant, whereby all the components are present in a fixed ratio with respect to one another. Also mentioned is that, a permanent shaping also implies a curling of the hair. However, a heat-treatment of the fiber is not mentioned within the scope of a permanent shaping.

In the publication US-A1-2003/0009834, formulations containing oxidizing agents, which are stable on storage, are obtained through the addition of a combination of at least one cationic polymer, at least one fatty alcohol, at least one ethoxylated fatty alcohol as well as at least one fatty acid amide.

The publication WO-A1-97/25964 discloses leave-on agents for conditioning the fibers containing keratin, which contain cationic polymers, especially polyquaternium-37. The use of these polymers in a special method for smoothing keratinous fibers is not mentioned.

The publication AU-A-596928 relates to permanent wave agents, which contain a protein hydrolysate and a silicone. According to the disclosure of this publication, the agents are exclusively used in a process waving the hair. The use of such permanent wave agents in a special method for smoothing the hair is not mentioned anywhere.

BRIEF SUMMARY OF THE INVENTION

A first object of the present invention is a method for smoothing fibers containing keratin, preferably human hair, wherein
(i) an aqueous composition (A), containing at least one keratin-reducing compound is applied to the fibers,
(ii) the aqueous composition (A) is rinsed away after a reaction time Z1,
(iii) optionally, the fibers are dried, and subsequently
(iv) the fibers are subjected to a heat-treatment with mechanical smoothing of the fiber at a temperature of 120-220° C.,
(v) subsequently, an aqueous composition (B) containing at least one oxidizing agent is applied to the fibers, and
(vi) said aqueous composition (B) is rinsed away after a reaction time Z2,
wherein at least one of the aqueous compositions (A) and (B) respectively, also contains at least one compound with a conditioning effect, said compound with conditioning effect being selected from amongst cationic polymers, quaternary ammonium compounds, silicones and protein hydrolyzates.

An aqueous composition according to the invention contains at least 50 wt. % of water with respect to the weight of the entire composition.

The mechanical smoothing implies a stretching of the curly hair along its longitudinal axis. This mechanical smoothing can be done, for instance, by means of a comb or a brush.

A further object of the invention is the use of at least one compound with a conditioning effect, selected from cationic polymers, quaternary ammonium compounds, silicones and protein hydrolyzates, in an aqueous composition (A) and/or (B) and, optionally (C) in a method in accordance with the first object of the invention. In this connection, the cationic polymers described below are used preferably.

The invention further provides a kit-of-parts, containing the previously defined aqueous compositions (A) and (B) and, optionally, a aqueous composition (C) as defined below, whereby each of the aqueous compositions are packed in separate containers.

DETAILED DESCRIPTION OF THE INVENTION

The heat treatment with mechanical smoothing of the fiber takes place at a temperature of 120-220° C., preferably at a temperature of 140-200° C. The heat treatment can be done with hot air. In this case, the hair is heated while combing exactly at the point where the mechanical smoothing is done. Furthermore, it is particularly preferred that the heat treatment is done according to the smoothing using appropriate tempered plates, especially metallic or ceramic plates, in which the plate is pressed on to the fiber to be smoothed and the plate pressed on the fiber is moved along the fiber. The plates can be coated with heat-resistant materials. Preferably, the fiber containing keratin to be smoothed is pressed between two appropriately tempered plates and both plates are moved simultaneously along the longitudinal axis of the fiber. More preferably, both plates are joined with each other, so that both plates can be moved uniformly along the fiber. The movement along the fiber takes place along the longitudinal axis of the fiber. If the hair of a living human being is heat-treated, then the fiber is fixed at one end (hair root). The plates in this case are moved uniformly away from the hair root along the entire fiber. This movement results in a mechanical smoothing of the fiber. An appropriate device for heat treatment is, for instance, the device "Ceramic Flat-Master" (marketed by Efalock, Germany).

A dry fiber containing keratin as in step (iii) of the method according to the invention is present, when the water residue adhering to the hair is evaporated to such an extent that the hair separates out. In the case of a dry fiber containing keratin, it is preferred that the moisture content of the fiber is either in equilibrium with the moisture content of the air or else the fiber absorbs the moisture from the surrounding air. Such a dry fiber is preferably achieved by drying the wet fiber with hot air from a hair dryer. Step (iii) is carried out preferably if the heat treatment in step (iv) is done through smoothing, e.g., with appropriately tempered plates.

In an especially preferred embodiment, the fibers containing keratin are moistened before step (i). This can be done by spraying the fiber with a liquid, preferably water. Preferably, the fibers are shampooed with a commercial shampoo before step (i), rinsed and then wiped with a towel. After the wiping is complete, a certain residual amount of moisture remains on the hair.

It is preferred to mechanically smooth the fibers directly after the step (i) and/or during the reaction time Z1 in step (ii) and optionally directly before step (iv). In a preferred embodiment of the invention, an aqueous composition (C) is applied to the fiber in step (ii) after the reaction time Z1. This aqueous composition (C) contains at least one compound with a conditioning effect, selected from amongst cationic polymers, quaternary ammonium compounds, silicones and protein hydrolysates and after a reaction time Z3 the aqueous compositions (A) and (C) are rinsed away. According to the method of the present invention it is preferred to rinse the fibers after a reaction time Z1, then apply the aqueous composition (C) and rinse again after a reaction time Z3. Preferably, the aqueous composition (C) additionally contains a cationic polymer. Further, the aqueous composition (C) is preferably formulated as an emulsion, especially as oil-in-water emulsion. For this purpose, the aqueous composition (C) preferably contains the common components, such as $C_8$-$C_{30}$ fatty alcohols and emulsifiers.

Emulsifiers according to the invention are described below.

Although the aqueous composition (C) is rinsed away from the hair and the hair is dried before step (iv), the use of the aqueous composition (C) is advantageous for the hair during the heat treatment. If the heat treatment is conducted by using tempered metal plates, the pre-treatment of the fiber with the aqueous composition (C) improves the sliding movement of the metal plates along the hair fiber as well as reduces the electrostatic charging of the hair, although the aqueous composition (C) has been rinsed away thoroughly.

The reaction time Z1 is preferably 5-60 minutes, especially preferred 10-30 minutes. The reaction time Z2 is preferably 1-30 minutes, especially preferred 5-20 minutes. The reaction time Z3 is preferably 1 second to 60 minutes, especially preferred 30 seconds to 5 minutes.

In a preferred embodiment of the method according to the invention, the aqueous composition (A) contains at least two compounds with a conditioning effect, selected from amongst cationic polymers, quaternary ammonium compounds, silicones and protein hydrolysates. Preferably, two different representatives are selected from the group of the above-mentioned compounds having a conditioning effect. According to the invention, it is especially preferred, that the aqueous composition (A) contains at least a protein hydrolysate and at least a silicone as compounds with a conditioning effect.

Further, it is preferred that the aqueous composition (B) contains at least one cationic polymer as the compound with a conditioning effect. The keratin reducing compounds contained in the aqueous composition (A) are selected preferably from amongst the compounds with at least one thiol group as well as their derivatives, and from among sulfites, hydrogen sulfites and disulfites.

Compounds with at least one thiol group and their derivatives are, for instance, thioglycolic acid, thiolactic acid, thiomalic acid, phenylthioglycolic acid, mercaptoethane sulfonic acid as well as their salts and esters (such as isooctylthioglycolate and isopropylthioglycolate), cysteamine, cysteine, Bunte salts and salts of the sulphuric acid. Especially suitable are the monoethanolammonium salts or ammonium salts of thioglycolic acid and/or thiolactic acid as well as the free acids. These are used in the aqueous composition (A) preferably in concentrations of 0.5 to 2.0 mol/kg at a pH-value between 5 to 12, especially between 7 to 9.5. For setting the pH value, the aqueous compositions (A) as per the invention normally contain alkalizing agents such as ammonia, alkali and ammonium carbonate and hydrogen carbonate or organic amines like monoethanolamine.

Examples of disulfite keratin reducing compounds, which may be present in the aqueous composition (A), are alkali disulfites, such as sodium disulfite ($Na_2S_2O_5$) and potassium disulfite ($K_2S_2O_5$), as well as magnesium disulfite and ammonium disulfite (($NH_4)_2S_2O_5$). Ammonium disulfite may be preferred according to the invention.

Examples of keratin reducing compounds of hydrogen sulfite, which may be present in the aqueous composition (A), are hydrogen sulfite as alkali-, magnesium-, ammonium- or alkanolammonium-salt based on a $C_2$-$C_4$-mono-, di- or trialkanolamine. Ammonium hydrogen sulfite can be the especially preferred hydrogen sulfite. Examples of keratin reducing sulfite compounds which may be present in the aqueous composition (A), are sulfites such as alkali-, ammonium or alkanolammonium-salt based on a $C_2$-$C_4$-mono-, di- or trialkanolamine.

Ammonium sulfite is preferred. The pH of the aqueous composition (A), when using sulfite and/or disulfite and/or hydrogen sulfite, is preferably in the neutral pH range 5 to 8, preferably 6 to 7.5.

Preferred $C_2$-$C_4$-alkanolamines are, as per the invention, 2-aminoethanol(monoethanolamine) and N,N,N-tris(2-hydroxyethyl)amine(triethanolamine). Monoethanolamine is an especially preferred $C_2$-$C_4$-alkanolamine, which is used especially in a quantity of 0.2 to 6 wt. % with respect to the entire aqueous composition (A).

The keratin reducing compound is preferably used in a quantity of 5 to 20 wt. %, with respect to the entire aqueous composition (A).

Moreover, the aqueous composition (A) can contain further components, which promote the effect of the keratin reducing compounds on keratin. Such components are, for instance, the swelling agents for fibers containing keratin, such as $C_1$-$C_6$ alcohols and water-soluble glycols or polyols such as glycerin, 1,2-propylene glycol or sorbite and urea or urea derivatives, such as allantoin and guanidine as well as imidazole and its derivatives. A preferred further component is 1,2-propylene glycol, particularly preferred in a quantity of 0.1 to 5 wt. %. In a preferred embodiment, the aqueous composition (A) as per the invention contains 0 to 5 wt. % of 1,2-propylene glycol and/or 0 to 5 wt. % of urea. Quantities specified refer to the complete aqueous composition of the compound (A).

Compounds having a conditioning effect according to the invention are preferably of the type of quaternary ammonium compounds such as, ammonium halogenides, especially chlorides and bromides, such as alkyl trimethyl ammonium halogenide, dialkyl dimethyl ammonium halogenide and trialkyl methyl ammonium halogenide, such as cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride, as well as the imidazolium compounds known under the INCI names of Quaternium-27, Quaternium-83 and Quaternium-87. The alkyl groups of the compounds mentioned above preferably have 10 to 18 carbon atoms.

The so-called esterquats also belong to the preferred quaternary ammonium compounds according to the invention. An esterquat is a substance, which contains at least one ester functional group in addition to the quaternary ammonium group in its structure. The preferred esterquats are quaternary ester salts of fatty acids with triethanolamine, quaternary ester salts of fatty acids with diethanol alkylamines and quaternary ester salts of fatty acids with 1,2-dihydroxypropyldialkyl amines. Such products, for instance are marketed under the trade marks of 'Stepantex®', 'Dehyquart®' and 'Armocare®'. The products Armocare® VGH-70, an N,N-bis(2-palmitoyloxyethyl)dimethyl ammonium chloride, as well as Dehyquart® F-75, Dehyquart® C-4046, Dehyquart® L80 and Dehyquart® AU-35 are examples of such esterquats.

Protein hydrolysates are product mixtures, which are obtained by acidic, basic or enzymatically catalysed hydrolysis of proteins. As per the invention, protein hydrolysates of plant as well as animal origin can be used.

Animal protein hydrolysates are, for instance, elastin-, collagen-, keratin-, silk- and milk protein hydrolysate, or their salts.

Such products are marketed under the brand names of Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

A preferred protein hydrolysate is the silk-protein hydrolysate (Promois® Silk 720, Promois® Silk 1000), which is preferably contained as conditioner compound, at least in the aqueous solution (A).

It is also in accordance with the invention to use protein hydrolysates of plant origin, such as for instance soya-, almond-, rice-, peas-, potato- and wheat protein hydrolysates. Such products are marketed under the trade marks Gluadin® (Cognis), DiaMin® (Diamalt), Lexein® (Inolex) and Crotein® (Croda).

It is also possible to use the derivatives of protein hydrolysates, for instance in the form of their fatty acid condensation products. Such products are marketed under the brand names Lamepon® (Cognis), Gluadin® (Cognis), Lexeinm® (Inolex), Crolastin® (Croda) or Crotein® (Croda).

Although the use of the protein hydrolysate as such is preferred, amino acid mixtures or individual amino acids and amino acid derivatives, such as arginine, asparagine, asparaginic acid, citrullin, histidine, ornithine, lysine and pyroglutaminic acid can also be used. The amino acids can be used as free amino acids as well as salts, such as hydrochloride or alkali, earth-alkali or ammonium salts.

Further, oligopeptides having an average of 2-3 amino acids, which have a high percentage (>50%, especially >70%) of the specified amino acid, can also be used according to the invention.

Especially preferred as per the invention are arginine, asparagine, asparaginic acid as well as their salts and oligopeptides or hydrolysates, which are rich in said amino acids. Especially preferred are asparagine and asparaginic acid as well as their salts or hydrolyzates.

In a preferred embodiment, the aqueous solution (C) is free from protein hydrolyzates.

Silicones that can be used as the conditioning compounds according to the invention are preferably linear, cyclic or branched silicones, selected from the types of cyclomethicones, dimethiconols, dimethiconcopolyols, amodimethicones, trimethyl silylamodimethicones and phenyltrimethicones. These silicone types are known to the expert under the nomenclature of the Cosmetic, Toiletry and Fragrance Association (CTFA) and are mentioned in: M. D. Berthiaume, Society of the Cosmetic Chemists Monograph Series, "Silicones in Hair Care", Ed.: L. D. Rhine, Publisher: Society of the Cosmetic Chemists, 1997, Chpt. 2, to which an explicit reference is made at this point.

Further examples are polysiloxanes such as dialkyl- and alkylaryl siloxanes, for instance, dimethyl polysiloxane and methylphenyl polysiloxane, as well as their alkoxylated analogs, analogs terminated with hydroxyl groups and quaternary analogs, as well as cyclic siloxanes. Thereby, especially the silicones with the INCI names Dimethicone, PEG-12 Dimethicone, PEG/PPG-18/18 Dimethicone, Cyclomethicone, Dimethiconol, Quaternium-80 and Amodimethicone as well as mixtures thereof are especially preferred silicones.

Examples of such silicones are the products marketed by Dow Corning under the names DC 190 (INCI name PEG/PPG-18/18 Dimethicone), DC 193 (INCI name: PEG-12 Dimethicone), DC200, DC1401 (INCI name: Cyclomethicone, Dimethiconol) and DC 1403 (INCI name: Dimethicone, Dimethiconol) as well as the trade products DC 244 (INCI name: Cyclomethicone), DC 344 (INCI name: Cyclomethicone) and DC 345 (INCI name: Cyclomethicone) of Dow Corning, Q2-7224 (manufacturer: Dow Corning; a stabilised trimethyl silylamodimethicone), Dow Corning 929 Emulsion (containing a hydroxyl-amino-modified silicone, which is also known as Amodimethicone), SM-2059 (Manufacturer: General Electric), SLM-55067 (Manufacturer: Wacker) as well as Abil Quat 3270 and 3272 (Manufacturer: Th. Goldschmidt; diquaternary polydimethylsiloxane, INCI name: Quaternium-80).

The cationic polymers are defined according to the invention as polymers having a group in the main and/or in the side chain, which can be "temporarily" or "permanently" cationic. The "permanently cationic polymers" are those which have a cationic group independently of the pH of the medium. These are usually polymers, which contain a quaternary nitrogen atom, for instance an ammonium group. Thus the preferred cationic groups are quaternary ammonium groups. Particularly preferred are polymers having a quaternary ammonium group bonded through a $C_1$-$C_4$ hydrocarbon group to a polymer main chain consisting of acrylic acid, methacrylic acid or their derivatives.

Particularly preferred are polymers having a structural element of the general formula (I),

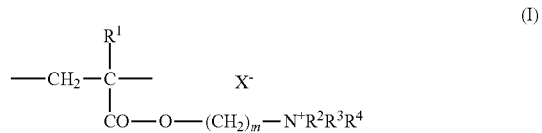

in which $R^1$ is a hydrogen atom or a methyl group, $R^2$, $R^3$ and $R^4$ are selected independently of one another from $C_1$-$C_4$-alkyl-, $C_2$-$C_4$-alkenyl- or $C_1$-$C_4$-hydroxyalkyl groups, m=1, 2, 3 or 4 and $X^-$ is a physiologically compatible organic or inorganic anion. The corresponding copolymers essentially consist of the structural elements given in formula (I) as well as nonionic monomer units.

Homopolymers made of the structural elements as per formula (I) are especially preferred cationic polymers.

Within the scope of these permanently cationic polymers with at least one structural unit as per formula (I), those polymers are preferred as per the invention, which satisfies at least one of the following conditions:

$R_1$ is a methyl group
$R_2$, $R_3$ and $R_4$ are methyl groups
m has the value 2.

Possible physiologically compatible counterions $X^-$ as per the formula (I), are for example the halogenide ions, sulphate ions, phosphate ions, methosulfate ions as well as organic ions such as lactate-, citrate-, tartrate- and acetate ions. Preferred are halogenide ions; particularly preferred is chloride.

An especially preferred homopolymer is, optionally crosslinked, poly(methacryloyl oxyethyl trimethyl ammonium chloride) with the INCI name Polyquaternium-37. The crosslinking can be done with polyolefinic unsaturated compounds, such as divinylbenzene, tetra-allyloxyethane, methylene bisacrylamide, diallylether, polyallylpolyglyceryl ether, or allylethers of sugars or sugar derivatives such as erythritol, pentaerythritol, arabitol, mannitol, sorbitol, sucrose or glucose. Methylene bis-acrylamide is a preferred crosslinking agent.

The homopolymer used is preferably in the form of a non-aqueous polymer dispersion, which should have a polymer content of not less than 30 wt. %. Such polymer dispersions are available in the market under the names of Salcare® SC 95 (approx. 50% polymer content, other components: mineral oil (INCI name: mineral oil) and tridecyl-polyoxypropylene-polyoxyethylene-ether (INCI name: PPG-1-Trideceth-6) and Rheocare® CTH (E) or Salcare® SC 96 (approx. 50% polymer content, other components: mixture of diesters of the propylene glycol with a mixture of capryl- and caprinic acid (INCI name: Propylene Glycol Dicaprylate/Dicaprate) and tridecyl polyoxypropylene-polyoxyethylene-ether (INCI name: PPG-1-Trideceth-6)).

Copolymers with the structural elements as per formula (I) contain as nonionic monomer units preferably acrylamide, methacryl amide, acrylic acid-$C_{1-4}$-alkyl ester and methacrylic acid-$C_{1-4}$-alkyl ester. Among these nonionic monomers, the acrylamide is especially preferred. These copolymers can, as described above in the case of the homopolymers, be crosslinked. A copolymer preferred as per the invention is the crosslinked acrylamide-methacryloyloxyethyl trimethyl ammonium chloride-copolymer. Such copolymers, in which the monomers are present in a weight ratio of about 20:80, are available in the market as approx. 50%-non-aqueous polymer dispersions under the name of Salcare® SC 92.

Other cationic polymers that can be used according to the invention are, for instance:

quaternary cellulose derivatives, as available in the market under the trade names Celquat® and Polymer JR®. The compounds Celquat® H 100, Celquat® L 200 and Polymer JR® 400 are preferred quaternary cellulose derivatives;

cationic alkylpolyglycosides as per the DE-PS 44 13 686;

cationized honey, for example the trade product Honeyquat® 50;

cationic guar derivatives, such as the ones available under the trade names Cosmedia® Guar and Jaguar®;

Polysiloxanes with quaternary groups such as the products available in the market under the names Q2-7224 (Manufacturer: Dow Corning; a stabilized trimethyl silyl amodimethicon), Dow Corning® 929 emulsion (containing a hydroxyl-amino-modified silicon, also known as amodimethicone), SM-2059 (Manufacturer: General Electric), SLM-55067 (Manufacturer: Wacker) as well as Abil®-Quat 3270 and 3272 (Manufacturer: Th. Goldschmidt), di-quaternary polydimethyl siloxane, Quaternium-80);

polymeric dimethyl diallyl ammonium salts and their copolymers with esters and amides of acrylic acid and methacrylic acid. The products available in the market under the names Merquat®100 (poly (dimethyl diallyl ammonium chloride)) and Merquat®550 (dimethyl diallyl ammonium chloride-acrylamide-copolymer) are examples of such cationic polymers;

Copolymers of vinyl pyrrolidones with quaternary derivatives of dialkyl aminoalkyl acrylate and -methacrylate, such as vinylpyrrolidone-dimethylamino ethyl-methacrylate-copolymers quaternized with diethyl sulfate. Such compounds are available in the market under the names Gafquat®734 and Gafquat®755;

Vinylpyrrolidone-vinylimidazolium-methochloride copolymers like the ones available under the names Luviquat® FC 370, FC 550, FC 905 and HM 552;

Quaternized polyvinyl alcohol;

as well as polymers known under the names Polyquaternium 2, Polyquaternium 17, Polyquaternium 18 and Polyquaternium 27 with quaternary nitrogen atoms in the polymer main chain.

Similarly, polymers known under the names of polyquaternium-24 (commercial product, e.g., Quatrisoft® LM 200) can be used as cationic polymers. In the same way, usable as per the invention are copolymers of vinylpyrrolidone such as the ones available in the market under the name Copolymer 845 (Manufacturer: ISP), Gaffix® VC 713 (Manufacturer: ISP), Gafquat® ASCP 1011, Gafquat® HS110, Luviquat® 81 55 and Luviquat® MS 370.

Other cationic polymers according to the invention are the so-called "temporary cationic" polymers. These temporary cationic polymers contain an amino group, which is present as quaternary ammonium group and hence cationic only at certain pH values.

Preferred are, for instance, Chitosan and its derivatives, such as the ones freely available in the market under the trade names Hydagen® CMF, Hydagen® HCMF, Hytamer® PC and Chitolam® NB/101.

Preferred cationic polymers as per the invention are the cationic cellulose derivatives and Chitosan and its derivatives, especially the commercial products Polymer® JR 400, Hydagen® HCMF and Kytamer® PC, cationic guar derivatives, cationic honey derivatives, especially the commercial product Honeyquat® 50, cationic alkylpolyglycosides as per the DE-PS 44 13 686 and polymers of the type Polyquaternium-37.

It is preferred according to the invention not to use any quaternary protein derivatives as cationic polymers within the scope of the invention.

Compounds with a conditioning effect used in the aqueous compositions according to the invention are preferably present in quantities of 0.01 to 10 wt. %, with respect to the entire composition. Quantities of 0.1 to 5 wt. % are especially preferred.

Furthermore, the aqueous compositions (A) and/or (B) and/or (C) used in the method according to the invention can contain at least one surface-active agent selected from among the group comprising anionic, amphoteric, zwitterionic and nonionic surfactants. The surfactants promote inter alia wetting of the keratin surface with the treatment solution.

As anionic surfactants in preparations according to the invention, in principle all the anionic surface active agents suitable for use on the human body can be used. These are characterized by a water-soluble, anionic group, such as a carboxylate-, sulfate-, sulfonate- or phosphate group and a lipophilic alkyl group with about 8 to 30 C atoms. In addition, glycol- or polyglycolether-groups, ester-, ether- and amide groups as well as hydroxyl groups may be present in the molecule. Examples of suitable anionic surfactants are, respectively in the form of sodium-, potassium- and ammonium- as well as mono-, di- and trialkanol ammonium salts with 2 to 4 C atoms in the alkanol group, linear and branched fatty acids with 8 to 30 C atoms (soaps), ether carboxylic acids of the formula $R-O-(CH_2-CH_2O)_x-CH_2-COOH$, in which R is a linear alkyl group with 8 to 30 C atoms and x=0 or 1 to 16, acylsarcosides with 8 to 24 C atoms in the acyl group, acyltaurides with 8 to 24 C atoms in the acyl group, acylisethionates with 8 to 24 C atoms in the acyl group, sulfosuccinic acid mono- and dialkyl-ester with 8 to 24 C atoms in the alkyl group and sulfosuccinic acid monoalkyl polyoxyethyl ester with 8 to 24 C atoms in the alkyl group and 1 to 6 oxyethyl groups, linear alkanesulfonates with 8 to 24 C atoms, linear alpha-olefin sulfonates with 8 to 24 C atoms, alpha-sulfo fatty acid methylester of fatty acids with 8 to 30 C atoms, alkyl sulfates and alkyl polyglycol ether sulfates of the formula $R-O(CH_2-CH_2O)_x-OSO_3H$, in which R is a preferably linear alkyl group with 8 to 30 C atoms and x=0 or 1 to 12, mixed surface-active hydroxyl sulfonates as per DE-A-37 25 030, sulfated hydroxy-alkylpolyethylene- and/or hydroxy-alkylene propylene glycol ether as per DE-A-37 23 354, sulfonates of unsaturated fatty acids with 8 to 24 C atoms and 1 to 6 double bonds as per DE-A-39 26 344, esters of tartaric acid and citric acid with alcohols, which represent the addition products of about 2-15 molecules of ethylene oxide and/or propylene oxide with fatty alcohols with 8 to 22 C atoms, alkyl- and/or alkenylether phosphate of the formula (E1-I),

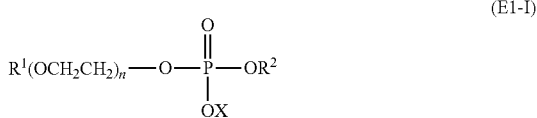
(E1-I)

in which $R^1$ preferably stands for an aliphatic hydrocarbon group with 8 to 30 carbon atoms, $R^2$ for hydrogen, a group $(CH_2CH_2O)_nR^1$ or X, n for numbers from 1 to 10 and X for hydrogen, an alkali- or earth-alkali metal or $NR^3R^4R^5R^6$, wherein $R^3$ to $R^6$ are independently of one another hydrogen or a C1 to C4 hydrocarbon group;

sulfated fatty acid alkylene glycol ester of the formula (E1-II)

$R^7CO(AlkO)_nSO_3M$ (E1-II)

wherein $R^7CO$— stands for a linear or branched, aliphatic, saturated and/or unsaturated acyl group with 6 to 22 C atoms, Alk for $CH_2CH_2$, $CHCH_3CH_2$ and/or $CH_2CHCH_3$, n for numbers from 0.5 to 5 and M for a cation, as described in DEOS 197 36 906.5;

Monoglyceride sulfates and monoglyceride ether sulfates of the formula (E1-III)

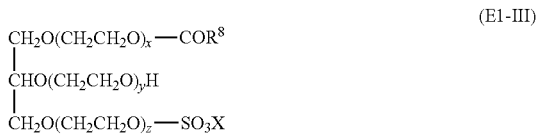
(E1-III)

wherein $R^8CO$ stands for a linear or branched acyl group with 6 to 22 carbon atoms, x, y and z in the total for 0 or for numbers from 1 to 30, preferably 2 to 10, and X for an alkali- or earth-alkali metal. Typical examples of suitable monoglyceride (ether) sulfates in the sense of the invention are the conversion products of laurinic acid monoglyceride, coconut oil monoglyceride, palmitic acid monoglyceride, stearic acid monoglyceride, oleic acid monoglyceride and sebum oil acid monoglyceride as well as their ethylene oxide adducts with sulfur trioxide or chlorosulfonic acid in the form of their sodium salts. Preferably, the monoglyceride sulfates of the formula (E1-III) are used, in which $R^8CO$ stands for a linear acyl group with 8 to 18 carbon atoms, such as the ones described in EP-B1 0 561 825, EP-B1 0 561 999, DE-A1 42 04 700 or by A. K. Biswas et al. in *J. Am. Oil. Chem. Soc.*, 37, 171 (1960) and F. U. Ahmed in *J. Am. Oil. Chem. Soc.*, 67, 8 (1990);

amide-ether carbonic acids, as described in EP 0 690 044;

condensation products of $C_8$-$C_{30}$-fatty alcohols with protein hydrolysates and/or amino acids and their derivatives, known to experts as protein fatty acid condensates, such as the Lamepon® types, the Gluadin® types, Hostapon® KCG or the Amisoft® types.

Preferred anionic surfactants are alkyl sulfates, alkyl polyglykol ether sulfates and ether carbonic acids with 10 to 18 C atoms in the alkyl group and up to 12 glycol ether groups in the molecule, sulfosuccinic acid mono- and -dialkyl-ester with 8 to 18 C atoms in the alkyl group and sulfosuccinic acid mono-alkyl polyoxyethyl ester with 8 to 18 C-atoms in the alkyl group and 1 to 6 oxyethyl-groups, monoglycerdisulfate, alkyl- and alkenyl-ether phosphate as well as protein fatty acid condensates.

Zwitterionic surfactants are such surface-active compounds, which carry at least one quaternary ammonium group and at least one $—COO^{(-)}$ or $—SO_3^{(-)}$ group in the molecule. Especially suitable zwitterionic surfactants are the so-called betaines, like the N-alkyl-N,N-dimethyl ammonium-glycinate such as cocoalkyl-dimethyl ammonium glycinate, N-acyl-aminopropyl-N,N dimethyl ammonium glycinate such as cocoacylamino-propyl-dimethyl-ammonium glycinate, and 2-alkyl-3-carboxymethyl-3-hydroxyethyl-imidazoline each with 8 to 18 C atoms in the alkyl- or acyl group, as well as coco-acylaminoethyl-hydroxyethyl-carboxymethyl-glycinate.

A preferred zwitterionic surfactant is the fatty acid-amide derivative known under the INCI name of cocamidopropyl betaine.

Ampholytic surfactants are such surface-active compounds, which, apart from a $C_8$-$C_{24}$-alkyl- or -acyl group in the molecule, contain at least one free amino group and at least one $—COOH—$ or $—SO_3H$-group and are capable of forming internal salts. Examples of suitable ampholytic surfactants are N-alkyl-glycine, N-alkyl-propionic acids, N-alkyl-aminobutyric acids, N-alkyl-iminodipropionic acids, N-hydroxyethyl-N-alkyl-amidopropyl glycine, N-alkyltaurine, N-alkylsarcosine, 2-alkyl-aminopropionic acids and alkyl-aminoacetic acids each with about 8 to 24 C atoms in the alkyl group. Especially preferred ampholytic surfactants are N-cocalkylaminopropionate, cocacylaminoethylaminopropionate and $C_{12}$-$C_{18}$-acylsarcosine.

Nonionic surfactants contain as the hydrophilic group, e.g., a polyolic group, a poly-alkylene glycol-ether-group or a combination of polyolic- and polyglycol-ether group. Such compounds are, for instance addition products of 2 to 50 mole ethylene oxide and/or 0 to 5 mole propylene oxide with linear and branched fatty alcohols having 8 to 30 C atoms, with fatty acids having 8 to 30 C atoms and with alkylphenols with 8 to 15 C atoms in the alkyl group, with a methyl- or $C_2$-$C_6$-alkyl group end-group-terminated addition products of 2 to 50 mole ethylene oxide and/or 0 to 5 mole propylene oxide with linear and branched fatty alcohols having 8 to 30 C atoms, with fatty acids having 8 to 30 C atoms and with alkyl phenols having 8 to 15 C atoms in the alkyl group, such as the types available under the brand names of Dehydol® LS, Dehydol® LT (Cognis), $C_{12}$-$C_{30}$-fatty acid mono- and diesters of addition products of 1 to 30 mole ethylene oxide and glycerin, addition products of 5 to 60 mole ethylene oxide with castor oil and hydrolyzed castor oil, polyolic-fatty acid esters, such as the commercial product Hydagen® HSP (Cognis) or Sovermol-types (Cognis), alkoxylated triglycerides, alkoxylated fatty acid alklyesters of the formula (E4-I)

$R^1CO—(OCH_2CHR^2)_wOR^3$ (E4-I)

in which $R^1CO$ stands for a linear or branched, saturated and/or unsaturated acyl group with 6 to 22 carbon atoms, $R^2$ for hydrogen or methyl, $R^3$ for linear or branched alkyl groups with 1 to 4 carbon atoms and w stands for numbers from 1 to 20, amine oxides, hydroxymixed ethers, like the ones described in DE-OS 19738866, sorbitan fatty acid ester and addition products of ethylene oxide with sorbitan fatty acid ester, such as the polysorbate, sugar fatty acid ester and addition products of ethylene oxide with the sugar fatty acid ester, addition products of ethylene oxide with fatty acid alcohol amides and fatty amines, sugar surfactants of the type of alkyl- and alkenyl-oligoglycoside as per the formula (E4-II), $$R^4O\text{-}[G]_p \qquad \text{(E4-II)}$$

in which $R^4$ stands for an alkyl- or alkenyl-group with 4 to 22 carbon atoms, G stands for a sugar group with 5 or 6 carbon atoms and p for numbers between 1 and 10. These can be obtained by the relevant methods of the preparative organic chemistry. As an example for the comprehensive literature the review work done by Biermann et al. in *Starch*, Vol. 45, p. 281 (1993), B. Salka in *Cosm. Toil.*, Vol. 108, p. 89 (1993) as well as J. Kahre et al. in *SOFW-Journal*, Vol. 8, p. 598 (1995) are mentioned here.

Alkyl- and alkenyl-oligoglycosides can be derived from aldoses or ketoses with 5 or 6 carbon atoms, preferably from glucose. Preferred alkyl- and/or alkenyl-oligoglycosides are thus alkyl- and/or alkenyl-oligoglucoside.

The index number p in general formula (E4-II) specifies the degree of oligomerization (DP), i.e., the distribution of mono- and oligoglycosides and stands for a number between 1 and 10. While p must always be an integer in the individual molecules and can take up the values p=1 to 6, the value of p for a specific alkyl-oligoglycoside is an analytically determined mathematical quantity, which mostly represents a fractional number. Preferably, the alkyl- and/or alkenyl-oligoglycosides are used with an average degree of oligomerization p of 1.1 to 3.0. From a technical viewpoint, such alkyl- and/or alkenyl-oligoglycosides are preferred, whose degree of oligomerization is less than 1.7 and lies especially between 1.2 and 1.4. The alkyl- or the alkenyl-group $R^4$ can be derived from the primary alcohols with 4 to 11, preferably 8 to 10 carbon atoms. Typical examples are butanol, hexyl alcohol, capryl alcohol, caprin alcohol and undecyl alcohol as well as mixtures thereof, like the ones obtained during the hydration of fatty acid methyl esters or during the hydration of aldehydes Roelen's oxo-synthesis. Preferred are the alkyl oligoglucosides with the chain length $C_8$-$C_{10}$ (DP=1 to 3), which are produced as forerunners in the distillative separation of Ca-Cla-coconut oil alcohol and may have by way of impurity a content of less than 6 wt. % of C12 alcohol, as well as alkyl oligoglucoside based on technical $C_{9/11}$-oxoalcohols (DP=1 to 3). The alkyl- or the alkenyl-group RI5 can further be derived also from the primary alcohols with 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as technical mixtures thereof, which can be obtained as described above. Preferred are the alkyl oligoglucosides based on hydrolyzed $C_{12/14}$-cocoalcohol with a DP of 1 to 3.

Sugar surfactants of the type of fatty acid —N-alkyl-polyhydroxyalkylamide, a nonionic surfactant of the formula (E4-III), $$R^5CO\text{-}NR^6\text{-}[Z] \qquad \text{(E4-III)}$$

in which the $R^5CO$ stands for an aliphatic acyl group with 6 to 22 carbon atoms, $R^6$ is hydrogen, an alkyl- or hydroxyalkyl group with 1 to 4 carbon atoms and [Z] stands for a linear or branched poly-hydroxyalkyl group with 3 to 12 carbon atoms and 3 to 10 hydroxyl groups. The fatty acid N-alkyl-polyhydroxyalkylamides are known compounds, which normally can be obtained by a reductive animation of a reducing sugar with ammonia, an alkylamine or an alkanolamine and subsequent acylation with a fatty acid, a fatty acid alkyl ester or a fatty acid chloride.

Regarding the methods for their preparation, reference is made here to U.S. patent specifications U.S. Pat. No. 1,985, 424, U.S. Pat. No. 2,016,962 and U.S. Pat. No. 2,703,798 as well as International Patent Publication No. WO 92/106984. An overview on this subject by H. Kelkenberg is given in *Tens. Surf. Det.*, Vol. 25, p. 8 (1988). Preferably, the fatty acid N-alkyl-polyhydroxyalkylamides are derived from reducing sugars with 5 or 6 carbon atoms, especially from glucose. The preferred fatty acid N-alkyl-polyhydroxyalkylamides thus represent fatty acid N-alkylglucamides, as given by the formula (E4-IV):

$$R^7CO\text{-}NR^8\text{-}CH_2\text{-}(CHOH)_4CH_2OH \qquad \text{(E4-IV)}$$

Preferably, glucamides of the formula (E4-IV) are used as fatty acid N-alkyl-polyhydroxyalkylamides, in which $R^8$ stands for hydrogen or an alkyl group and $R^7CO$ stands for the acyl group of the capronic acid, caprylic acid, caprinic acid, laurinic acid, myristinic acid, palmitic acid, palmoleic acid, stearic acid, isostearic acid, oleic acid, elaidinic acid, petroselinic acid, linoleic acid, linolenic acid, arachinic acid, gadoleinic acid, behenic acid or erucanic acid or technical mixtures thereof. Especially preferred are fatty acid N-alkyl-glucamides of the formula (E4-IV), which are obtained by the reductive amination of glucose with methylamine and subsequent acylation with laurinic acid or $C_{12/14}$-coconut fatty acid or an appropriate derivative. Further, the polyhydroxyalkylamides can also be derived from maltose and palatinose.

Alkylene oxide addition products with the saturated linear fatty alcohols and fatty acids having 2 to 30 mole ethylene oxide per mole of fatty alcohol or fatty acids have proved to be the preferred nonionic surfactants. Preparations with excellent properties are also obtained, if these contain the fatty acid esters of ethoxylated glycerin as the nonionic surfactant.

These compounds can be characterized by the following parameters. The alkyl group contains 6 to 22 carbon atoms and can be linear as well as branched. Preferred are the primary linear and in 2-position methyl-branched aliphatic groups.

Such alkyl groups are, for instance 1-octyl, 1-decyl, 1-lauryl, 1-myristyl, 1-cetyl and 1-stearyl. Especially preferred are 1-octyl, 1-decyl, 1-lauryl, 1-myristyl. When using the so-called "oxo alcohols" as the starting substances, a majority of compounds with an odd number of carbon atoms are present in the alkyl chain.

Further, the sugar surfactants may also be present as the nonionic surfactants in the compositions (A), (B) and/or (C). In the compositions used as per the invention, these may be present preferably in quantities of 0.1-20 wt. %, with respect to the respective complete composition. Quantities of 0.5-15 wt. % are preferred, and especially preferred are the quantities of 0.5-7.5 wt. %.

The used surfactants with alkyl groups can be uniform substances. However, normally it is preferred to start with the native animal and plant materials when preparing these substances, so that one gets mixtures with different lengths of the alkyl chains, depending upon the respective raw material.

Regarding the surfactants being addition products of ethylene- and/or propylene oxide with fatty alcohols or derivatives of these addition products, one may use products with a "normal" homologous distribution as well as such with a limited homologous distribution. "Normal" homologous distribution means mixtures of homologues, which one gets by the conversion of fatty alcohols and alkylene oxide using alkali metals, alkali metal hydroxides or alkali metal alcoholates as catalysts. On the other hand, limited homologous distribution is obtained, when, for instance, hydrotalcite, earth-alkali metals of ether carbonic acids, earth-alkali metal oxides, -hydroxides or alcoholates are used as catalysts. The use of products with a limited homologous distribution can be of advantage.

The surfactants are used in quantities of 0.1-45 wt. %, preferably 0.5-30 wt. % and especially preferred in quantities of 0.5-25 wt. %, with respect to the entire composition according to the invention.

In a further embodiment, emulsifiers are used in the aqueous compositions (A) and/or (B) and/or (C) of the method according to the invention.

Emulsifiers effect the formation of water- or oil-stable adsorption layers at the phase interface, which prevent the dispersed droplets from coalescing and hence stabilize the emulsion. Emulsifiers, like surfactants, are made up of one hydrophobic and one hydrophilic molecule. Hydrophilic emulsifiers preferably form the O/W-emulsions and hydrophobic emulsifiers preferably form the W/O emulsions. An emulsion is a drop-shaped distribution (dispersion) of one liquid in another liquid by expending energy for creating a stabilized phase interface with the help of surfactants. The selection of these emulsifying surfactants or the emulsifiers is based on the substance to be dispersed and the respective outer phase as well as the droplet size of the emulsion. Further definitions and properties of the emulsifiers are given in "H. D. Dorfler, *Surface and Colloidal Chemistry*, VCH Publishing House GmbH, Weinheim, 1994". Emulsifiers that can be used as per the invention are for instance

- addition products of 4 to 100 mole ethylene oxide and/or 0 to 5 mole propylene oxide with linear fatty alcohols with 8 to 22 C atoms, with fatty acids with 12 to 22 C atoms and with alkyl phenols with 8 to 15 C atoms in the alkyl group.
- $C_{12}$-$C_{22}$-fatty acid mono- and diester of addition products of 1 to 30 mole ethylene oxide with polyols with 3 to 6 carbon atoms, especially with glycerin.
- ethylene oxide and polyglycerin addition products with methyl glucoside fatty acid ester, fatty acid alkanolamide and fatty acid glucamide.
- $C_8$-$C_{22}$-alkylmono- and -oligoglycosides and their ethoxylated analogs, whereby the degree of oligomerization is from 1.1 to 5, especially 1.2 to 2.0, and glucose is preferred as sugar component.
- mixtures of alkyl-(oligo)-glucosides and fatty alcohols, for example the product Montanov® 68, available in the market.
- addition products of 5 to 60 mole ethylene oxide with castor oil and hydrolyzed castor oil.
- partial ester of polyols with 3-6 carbon atoms with saturated fatty acids with 8 to 22 C atoms.
- sterols. Sterols imply a group of steroids, which carry a hydroxyl group at the C-3 atom of the steroid backbone and are isolated from animal tissue (zoosterols) as well as from plant fats (phytosterols) or mycosterols. Examples of zoosterols are cholesterol and lanosterol. Examples of phytosterols are ergosterol, stigmasterol and sitosterol. The so-called mycosterols are also isolated from mushrooms and yeasts.
- phospholipids. These mainly include the glucose phospholipids, which are represented, e.g., by lecithins or phosphatidylcholins extracted from egg yolk or plant seeds (e.g., soybeans).
- fatty-acid esters from sugar and sugar alcohols, such as sorbitol.
- polyglycerins and polyglycerin derivates, such as polyglycerin poly-12-hydroxyl stearate (trade name Dehymuls® PGPH).
- linear and branched fatty acids with 8 to 30 C atoms and their Na-, K-, ammonium-, Ca-, Mg- and Zn-salts.

Compositions according to the invention contain the emulsifiers preferably in quantities of 0.1-25 wt. %, especially 0.1-3 wt. %, with respect to the entire composition.

Preferably, the aqueous compositions (A) and/or (B) and/or (C) according to the invention contain at least one nonionic emulsifier with an HLB value of 8 to 18, as per the definition mentioned in the Rompp-Lexicon Chemistry (Editor J. Falbe, M. Regitz), $10^{th}$ Ed., Georg Thieme Publisher Stuttgart, N.Y., p. 1764 (1997). Nonionic emulsifiers with an HLB value of 10-15 are especially preferred according to the invention.

Aqueous compositions (A) and/or (B) and/or (C) according to the invention preferably contain at least one linear or branched, saturated or unsaturated fatty alcohol. Fatty alcohols with $C_6$-$C_{30}$-, preferably $C_{10}$-$C_{22}$- and especially preferred $C_{12}$-$C_{22}$-carbon atoms can be used as fatty alcohols.

Usable in the sense of the invention are, for instance decanol, octanol, octenol, dodecenol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, capryl alcohol, caprin alcohol, linoleyl alcohol, linolenyl alcohol and behenyl alcohol, as well as their Guerbet alcohols, this listing being representative in nature and not restricted to above-mentioned compounds. The fatty alcohols, however, are preferably derived from natural fatty acid esters, wherein the fatty alcohol can be obtained from the esters of the fatty acids by hydrolysis.

According to the invention, such fatty alcohols can also be used, which are produced from the hydrolysis of naturally occurring triglycerides such as beef tallow, palm oil, groundnut oil, colza oil, cotton seed oil, soya oil, sunflower oil and linseed oil or from the esterification products with corresponding alcohols, and hence represent a mixture of different fatty alcohols.

Such substances can be purchased in the market, for instance, under the names Stenol®, e.g., Stenol® 1618 or Lanette®, e.g. Lanette® or Lorol®, e.g., Lorol® C8, Lorol® C14, Lorol® C18, Lorol® C8-18, HD-Ocenol®, Crodacol®, e.g., Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Naturally, lanolin alcohols, such as those available in the market under the brand names of Corona®, White Swan®, Coronet® or Fluilan® can also be used according to the invention.

The fatty alcohols are used in quantities of 0.1-20 wt. %, with respect to the entire composition, preferably in quantities of 0.1-10 wt. %.

The aqueous compositions (A) and/or (B) and/or (C) according to the invention, especially the aqueous compositions (A) and/or (B) preferably contain a viscosity-enhancing compound, hereinafter referred to as thickening agent.

Thickening agents that can be used according to the invention are, for instance, agar-agar, guar-gum, alginate, xanthan gum, Arabic gum, Karaya gum, carob-seed gum, linseed gum, dextrane, dicaprylate, dicaprate, cellulose derivatives, e.g., methyl cellulose, hydroxyalkyl cellulose and carboxymethyl cellulose, starch fractions and derivatives like amylose, amylopectin and dextrins, clays, such as bentonite or fully synthetic hydrocolloids, such as polyvinyl alcohol, as well as viscosity-enhancing polymers based on polyacrylate, such as the ones marketed under the trade names of Pemulen®, Aculyn® and Carbopol®.

The aqueous composition (A) preferably possesses a viscosity of 5,000 to 50,000 mPas, especially of 8,000 to 20,000 mPas, at 20° C. (measured using a Brookfield Viscometer, spindle No. 6 at 20 rpm).

The aqueous composition (B) possesses preferably a viscosity of 1,000 to 30,000 mPas, especially 2,000 to 10,000 mPas, at 20° C. (measured using a Brookfield Viscometer, spindle No. 4 at 20 rpm).

The oxidizing agent contained in the aqueous composition (B) is selected preferably from sodium bromate, potassium bromate or hydrogen peroxide. It is especially preferred to use hydrogen peroxide as the oxidizing agent. For stabilizing the hydrogen peroxide preparations, additional commercial stabilizers can also added. The pH value of the aqueous $H_2O_2$ preparations, which normally contain about 0.5 to 3.0 wt. % of $H_2O_2$, preferably lies between 2 and 6. Aqueous compositions (B) based on bromate normally contains the bromates in concentrations of 1 to 10 wt. % and have a pH value between 4 and 7.

Often, fixing compositions are used as solids for the permanent shaping of the fibers containing keratin. They then contain the oxidizing agent in the solid form, e.g., sodium perborate. Shortly before application water is added to these agents to form the aqueous composition (B).

Further, the following compounds can be contained in the aqueous compositions (A) and/or (B) and/or (C) used according to the invention:

linear and/or branched fatty acids, preferably $C_2$-$C_{30}$ fatty acids, especially preferred $C_4$-$C_{18}$ fatty acids, mostly preferred $C_6$-$C_{10}$ fatty acids and/or their physiologically compatible salts; further examples are formic acid, acetic acid, propionic acid, butyric acid, isobutyric acid, valeric acid, isovaleric acid, pivalinic acid, oxalic acid, malonic acid, succinic acid, glutaric acid, lactic acid, glyceric acid, glyoxylic acid, adipinic acid, pimelinic acid, suberic acid, azelaic acid, sebacic acid, propiolic acid, crotonic acid, isocrotonic acid, elaidinic acid, maleic acid, fumaric acid, muconic acid, citraconic acid, mesaconic acid, camphoric acid, benzoic acid, o,m,p-phthalic acid, naphthoic acid, toluoylic acid, hydratropic acid, atropic acid, cinnamic acid, isonicotinic acid, nicotinic acid, bicarbaminic acid, 4,4'-dicyano-6,6'-binicotinic acid, 8-carbamoyloctanic acid, 1,2,4-pentantricarbonic acid, 2-pyrrolcarbonic acid, 1,2,4,6,7-napthalin penta-carbonic acid, malonaldehydic acid, 4-hydroxy-phthalamidic acid, 1-pyrazol carbonic acid, gallic acid or propane-tricarbonic acid, polyhydroxy-compounds; the following are specially mentioned here sugar with 5 and/or 6 carbon atoms, especially as mono- and/or oligosaccharides, such as glucose, fructose, galactose, lactose, arabinose, ribose, xylose, lyxose, allose, altrose, mannose, gulose, idose, talose and sucrose and/or derivatives thereof, e.g., ether derivatives, amino derivatives and/or acetyl-derivatives like acetylated glucose, e.g., tetra-acetyl glucose, penta-acetyl glucose and/or 2-acetamido-2-deoxyglucose. Preferred sugar components are glucose, fructose, galactose, allose, lactose, arabinose and sucrose; glucose, galactose and lactose are especially preferred;

aldonic acids, especially gluconic acid, glucuronic acid;

polyols, such as glucamine, glycerin, mono- or diglycerides, 2-ethyl-1,3-hexandiol, 2-hydroxymethyl propantriol, glycols such as ethylene glycol, diethylene glycol, triethylene glycol, propylene glycol, dipropylene glycol, 1,3-butandiol;

polyhydroxylic acids, such as penta-hydroxyhexanic acid, tetra-hydroxypentanic acid and/or their derivatives, such as ether, ester and/or amides, e.g., penta-hydroxyhexanic acid amide and/or their physiologically compatible salts; other examples are: citric acid, malic acid or tartaric acid;

Pantolactone;

panthenol and/or its derivatives;

other vitamins, such as vitamin B6, C and/or E and/or their derivatives;

hydroxyl acids, such as .alpha.-.beta.-hydroxyl fatty acids or keto-fatty acids and/or their physiologically compatible salts; such as salicylic acid or lactic acid;

glyoxylic acid, glycolic acid;

water-soluble polymers with a fixing effect, e.g., polyvinyl pyrrolidon, vinyl acetate/crotonic acid copolymers;

anti-dandruff substances, such as picrotone olamine, zinc omadine;

active agents like allantoin, pyrrolidon carbonic acids, plant extracts;

pH-setting and buffering agents, such as citric acid/sodium citrate, ammonium carbonate, ammonium hydrogen carbonate, guanidine carbonate, phosphate;

complex-building agents, such as EDTA, NTA, organo-phosphonic acids, dipicolinic acid;

light protection agents (UV-absorber);

oil, fat and wax components, preferably in emulsion form;

colors, opacifiers and pearlescence agents, as well as aerosol propellants, if needed.

The examples given below explain in more detail the object of the invention:

EXAMPLES

TABLE 1

Smoothing creams

| Raw material | G1 [wt. %] | G2 [wt. %] | G3 [wt. %] | G-V1 [wt. %] | G-V2 [wt. %] |
|---|---|---|---|---|---|
| 1,2-propylene glycol | 2.00 | 1.00 | — | 2.00 | |
| Cetyl-stearyl alcohol[1] | 9.00 | 9.00 | 9.00 | 9.00 | 9.00 |
| Lanette ® E[2] | 0.50 | 0.50 | 0.50 | 0.50 | 0.50 |
| Brij ® 35 P[3] | 0.50 | 0.50 | 0.50 | 0.50 | 0.50 |
| Natrosol ® 250 HR 4 | 0.25 | 0.25 | 0.25 | 0.25 | 0.25 |
| Ammonia (25% aqueous solution) | 5.00 | 3.00 | 1.00 | 5.00 | 1.00 |
| Turpinal ® SL[5] | 0.25 | 0.25 | 0.25 | 0.25 | 0.25 |
| Ammonia thioglycolate (71% aqueous solution) | 18.00 | 13.00 | 8.00 | 18.00 | 8.00 |
| Ammonium bicarbonate | 4.00 | 0.30 | | 4.00 | |
| Promois ® Silk 1000[6] | 1.00 | | 1.00 | | |
| Promois ® Silk 720[7] | | 0.50 | | | |
| Dow Corning ® 1403 fluid[8] | 0.50 | 1.00 | 2.00 | | |
| Perfume | 1.00 | 1.00 | 1.00 | 1.00 | 1.00 |
| Water | Ad 100 | Ad 100 | Ad 100 | Ad 100 | Ad 100 |

[1]Mixture of 50 wt. % cetyl alcohol and 50 wt. % stearyl alcohol
[2]INCI Name: Sodium Cetearyl Sulphate (Cognis)
[3]Polyethylene glycol monolaurylether dodecanol with 23 mole-equivalent ethylene oxide (INCI Name: Laureth-23) (Uniquema)
[4]Hydroxyethyl cellulose (Hercules)
[5]1-Hydroxyethane-1,1-diphosphonic acid (INCI Name: Etidronic Acid, Aqua (Water)) (Solutia)
[6]Collagen hydrolysate (INCI Name: Hydrolized Silk) (RITA Corp.)
[7]Collagen hydrolysate (INCI Name: Hydrolized Silk) (RITA Corp.)
[8]INCI Name: Dimethicone, Dimethiconol (Dow Corning)

The smoothing creams, i.e., aqueous compositions (A) according to the method of the invention, carry the numbers G1, G2 and G3. The smoothing creams not in accordance with the invention carry the numbers G-V1 and G-V2.

TABLE 2

Holding agents

| Raw Material | Holding Agent No. | | | |
|---|---|---|---|---|
| | F1 [wt. %] | F2 [wt. %] | F3 [wt. %] | F-V1 [wt. %] |
| Cetearyl alcohol | 4.00 | 4.00 | 4.00 | 4.00 |
| Eumulgin ® B3 [9] | 0.50 | 0.50 | 0.50 | 0.50 |
| Ammonia (25% aqueous solution) | 0.80 | 0.80 | 0.80 | 0.80 |
| Dipicolinic acid | 0.10 | 0.10 | 0.10 | 0.10 |
| Turpinal ® SL [5] | 1.70 | 1.70 | 1.70 | 1.70 |
| Rheocare ® CTH(E) [10] | 1.00 | 1.00 | — | — |
| Genamin ® KDMP [11] | — | 2.00 | — | — |
| Merquat ® 100 [12] | — | — | 0.20 | — |
| Hydrogen peroxide (50% aqueous solution) | 4.00 | 4.00 | 4.00 | 4.00 |
| Water | Ad 100 | Ad 100 | Ad 100 | Ad 100 |

[9] Cetyl stearyl alcohol, ethoxylated with 30 units of ethylene oxide (INCI Name: Ceteareth-30) (Cognis)
[10] Trimethyl ammonio-ethyl methacrylate chloride homopolymer, (INCI Name: polyquaternium-37, propylene glycol dicaprylate/dicaprate, PPG-1 trideceth-6) (CRL Cosmetic Rheologies, Ltd.)
[11] Contains 85 wt. % C.sub.20-22-alkyl trimethyl ammonium chloride as active substance in isopropanol as solvent, (INCI Name: behentrimonium chloride) (Clariant)
[12] Poly (dimethyl diallyl ammonium chloride) (INCI Name: polyquaternium-6) (Nalco)

The holding agents, i.e. aqueous compositions (B) according to the method of the invention carry the numbers F1, F2 and F3. The holding agent which is not in accordance with the invention carries the number F-V1.

Performance of Tests for Hair Smoothing

In both the methods A and B given below, hair strands having a length of 30 cm and a weight of 2.8 g from naturally curly, untreated hair with a South-American origin of the company De Meo Brothers, New York, were used.

In a step involving intermediate and post-treatment, a rinsing in accordance with Table 3 was used in the methods A and B.

TABLE 3

Rinsing

| Material | Quantity in wt. % |
|---|---|
| Dehyquart ® F 75 [13] | 2.50 |
| Rewoquat ® W 575 PG [14] | 3.00 |
| Dehyquart ® A-CA [15] | 8.00 |
| Cetyl-stearyl alcohol | 8.00 |
| Glycerin monostearate | 0.50 |
| Isopropyl myristate | 3.00 |
| Ajidew ® NL-50 [16] | 0.50 |
| p-Hydroxybenzoic acid propylester | 0.15 |
| p-Hydroxybenzoic acid methylester | 0.15 |
| 2-Phenoxyethanol | 0.80 |
| Paraffin oil | 3.00 |
| Dow Corning ® 1403 fluid [8] | 0.75 |
| Salcare ® SC 96 [17] | 0.20 |
| Polymer JR 400 [18] | 0.50 |
| Tegoamid ® S 18 [19] | 2.00 |
| Nicotinic acid amide | 0.20 |
| D-Panthenol 75 W [20] | 0.50 |

TABLE 3-continued

Rinsing

| Material | Quantity in wt. % |
|---|---|
| Citric acid | 0.35 |
| Water | Ad 100 |

[13] Fatty alcohols methyl triethanolammonium methylsulphate dialkylester mixture (INCI Name: distearoylethyl hydroxyethylmonium methosulphate, cetearyl alcohol) (Cognis Germany)
[14] 1-Methyl-2-norpalmalkyl-3-palm fatty acid amidoethyl imidazolinium methosulphate, 75% active substance (INCI Name: quaternium-87, propylene glycol) (Goldschmidt)
[15] Trimethyl hexadecyl ammonium chloride, 25% active substance (INCI Name: Aqua (Water), Cetrimonium Chloride) (Cognis)
[16] Pyrrolidone carbonic acid sodium salt, 50% active substance, (INCI Name: Sodium PCA) (Ajinomoto)
[17] Trimethyl ammonioethyl methacrylate chloride homopolymer, (INCI Name: polyquaternium-37, propylene glycol dicaprylate/dicaprate, PPG-1 trideceth-6) (Ciba)
[18] Quaternary hydroxyl ethyl cellulose (INCI Name: polyquaternium-10) (Amerchol)
[19] N,N-dimethyl-N'-stearoyl-1,3-diaminopropane (INCI Name: stearamidopropyl dimethylamine) (Degussa)
[20] D-panthenyl alcohol, 75% active substance (BASF)

Method A

A1) The hair strands are colored with a commercial, ammonia-containing oxidizing hair color or by using hydrogen peroxide as the oxidizing agent. The hair is then washed with a commonly available shampoo and wiped with a towel.

A2) The hair strands are combed and 4.8 g of a smoothing cream (in accordance with Table 1 or 4) is applied with the help of a brush.

A3) After a reaction time Z1 of 20 minutes, the smoothing cream is thoroughly rinsed-off with water.

A4) 1.2 g of the rinsing in accordance with Table 3 is applied on the hair and is thoroughly rinsed-off with water after a reaction time of one minute.

A5) The hair strands are dried with the help of hot air by using a dryer, till the individual hairs separate and do not cling to one another owing to moisture.

A6) The strands are then smoothed mechanically with the help of the plates of the device "Ceramic Flat-Master" (Company Efalock, Germany), tempered to 180° C. For this purpose, the hair strand is passed between the plates of the device five times. The plates thereby apply a slight contact pressure on the hair.

A7) Subsequently, 5.3 g of a holding agent (in accordance with Table 2 or 4) are applied on to the strands and rinsed-off after a reaction time Z2 of 15 minutes.

A8) Thereafter, the strands are treated with 1.2 g of the rinse in accordance with Table 3 which is rinsed-off after a reaction time of 15 minutes.

Method B

B1) The hair strands are washed with a commercially available shampoo and are wiped with a towel.

B2) same as A2)

B3) After a reaction time Z1 of 30 minutes, the smoothing cream is rinsed thoroughly with water.

B4) same as A4)

B5) same as A5)

B6) same as A6)

B7) same as A7)

B8) same as A8)

The following methods were conducted with the following combinations of smoothing cream and holding agents:

TABLE 4

| | Smoothing (Experiment No.) | | | | |
|---|---|---|---|---|---|
| | 1 | 2 | 3 | 4 | 5 |
| Method | B | B | A | B | A |
| Smoothing cream (as per Table 1) | G1 | G2 | G3 | G-V1 | G-V2 |
| Holding agent (as per Table 2) | F | F2 | F3 | F-V1 | F-V1 |

The smoothing methods as per the invention carry the experiment numbers 1, 2, and 3 in accordance with Table 4. The smoothing methods in Table 4, having the experiment numbers 4 and 5, are in accordance with the invention and have been conducted for reference.

After the completion of the methods according to the invention, the hair were better and more uniformly smoothed and also better conditioned, in contrast to the methods not in accordance with the invention. The methods with the test numbers 1, 2 and 3 as per Table 4 also produce a hair, which is not electrostatically charged, whereas the hair produced by the smoothing methods not according to the invention possess an appreciable static charge.

We claim:

1. Method for smoothing keratin containing fiber comprising the steps of:
   (i) contacting the fiber with an aqueous composition (A) comprising at least one keratin-reducing compound, protein hydrolyzate and silicone;
   (ii) removing aqueous composition (A) after a reaction time of from 5 to 60 minutes;
   (iii) applying an aqueous composition (C) comprising at least one conditioning compound chosen from cationic polymers, quaternary ammonium compounds, silicones and protein hydrolyzates;
   (iv) removing aqueous composition (C) after a reaction time of from 1 second to 60 minutes;
   (v) drying the fibers;
   (vi) heating and mechanically smoothing the fibers from steps (ii), (iii), (iv) and/or (v) at a temperature of from 120 to 220° C.;
   (vii) contacting the fibers from step (iv) with an aqueous composition (B) comprising at least one oxidizing agent and Polyquaternium-37; and
   (viii) removing aqueous composition (B) after a reaction time of from 1 to 30 minutes.

2. Method of claim 1 wherein aqueous composition (A) comprises the keratin reducing compound in an amount of from 5 to 15 wt. %, based on total aqueous composition (A).

3. Method of claim 1 wherein aqueous composition (A) further comprises one or more anionic, nonionic, amphoteric or zwitterionic surfactants or combinations thereof.

4. Method of claim 1 wherein the quaternary ammonium compounds are chosen from alkyl trimethyl ammonium halogenides, dialkyl dimethyl ammonium halogenides, trialkyl methyl ammonium halogenides and esterquats.

5. Method of claim 1 wherein the silicones are chosen from cyclomethicones, dimethicones, dimethiconoles, dimethicone copolyoles, amodimethicones, trimethyl silylamodimethicones and phenyl trimethicones.

6. Method of claim 1 wherein the protein hydrolyzates are chosen from elastin, collagen, keratin, silk and milk protein hydrolyzates.

7. Method of claim 1 wherein aqueous composition (A) further comprises a cationic polymer containing at least one structural element of formula (I),

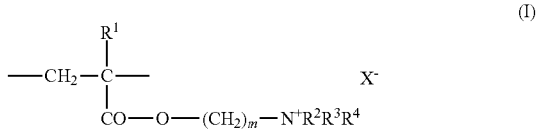

(I)

wherein $R^1$ is a hydrogen atom or a methyl-group, each of $R^2$, $R^3$ and $R^4$ is independently a $C_1$-$C_4$ alkyl group, $C_2$-$C_4$ alkenyl group or $C_1$-$C_4$ hydroxy-alkyl group, m=1, 2, 3 or 4, and $X^-$ is a physiologically compatible organic or inorganic anion.

8. Method of claim 1 wherein aqueous composition (A) 1 further comprises a cationic homopolymer.

9. Method of claim 1 wherein aqueous compositions (A) and/or (B) further comprise at least one viscosity-enhancing compound.

10. Method of claim 9 wherein aqueous composition (A) has a viscosity of from 5,000 to 50,000 mPas.

11. Method of claim 1 further comprising moistening the fiber before step (i).

12. Method of claim 1 further comprising mechanically smoothing the fiber during the reaction time of step (ii).

13. Method of claim 1 further comprising mechanically smoothing the fiber directly after step (i).

14. Method of claim 1 wherein step (vi) is carried out by pressing an at least one appropriately tempered plate on to the fiber and moving the plate along the fiber.

15. Method of claim 1 wherein the fiber is pressed between two plates while moving the plates along the fiber.

16. Method of claim 1 wherein aqueous composition (C) is applied after the reaction time for aqueous composition (A) and prior to removing aqueous composition (A), and wherein aqueous compositions (A) and (C) are removed after the reaction time of from 1 second to 60 minutes.

* * * * *